United States Patent [19]

Chan et al.

[11] 4,357,310

[45] Nov. 2, 1982

[54] METHOD AND COMPOSITION FOR REDUCING THE NONSPECIFIC BINDING OF RADIOIODINATED PROTEIN HORMONES

[75] Inventors: Catherine T. Chan, Lincoln; Debra A. Gravallese, Watertown, both of Mass.

[73] Assignee: Baxter Travenol Laboratories, Inc., Deerfield, Ill.

[21] Appl. No.: 176,820

[22] Filed: Aug. 8, 1980

[51] Int. Cl.$^3$ ............................................. A61K 43/00
[52] U.S. Cl. ..................................... 424/1; 23/230 B; 252/408; 424/12
[58] Field of Search ..................... 424/1, 12; 23/230 B; 252/408

[56] References Cited

U.S. PATENT DOCUMENTS 3,939,094  2/1976  Kauffman ........................... 424/1 X
3,997,470 12/1976  Monte et al. ........................ 252/408
4,107,284  8/1978  Sultanian et al. ..................... 424/1
4,124,527 11/1978  Kauffman ........................... 424/1 X
4,148,869  4/1979  Deaton ................................ 424/1

OTHER PUBLICATIONS

The Merck Index, 8th Edition, Merck & Co., Inc., N.J., 1968, pp. 848-849.
Friedman et al., "J. Clin. Micro." 9(1): 1-10 (1979).
De Savigny, "J. Clin. Path." 32: 284-288 (1979).
Cappel, "Arch. Virol." 58: 253-258 (1978).

Primary Examiner—Christine M. Nucker
Attorney, Agent, or Firm—Max D. Hensley; Lawrence W. Flynn; Paul C. Flattery

[57] ABSTRACT

Nonspecific binding of radioiodinated protein hormones in specific-receptor binding assays is reduced by including a nonionic detergent with the tracer during storage prior to the assay.

19 Claims, No Drawings

METHOD AND COMPOSITION FOR REDUCING THE NONSPECIFIC BINDING OF RADIOIODINATED PROTEIN HORMONES

BACKGROUND OF THE INVENTION

This invention relates to methods for determining proteins in biological samples using immobilized specific receptors for the proteins. In particular it relates to the reduction of nonspecific binding of radioiodine labelled protein hormones (tracers) in such methods.

Nonspecific binding is defined as the radioactivity found in the solid phase of a heterogenous assay conducted without antibody to the analyte in question. The interactions which are responsible for this phenomenon have not been fully elucidated. It is desirable to reduce the non-specific binding to as low a level as possible because the assay sensitivity and accuracy are otherwise adversely affected.

Protein harmones such as prolactin are relatively low molecular weight substances, on the order of 8,000 to 80,000 MW. They are well-known and largely fully characterized. Examples include, in addition to prolactin, insulin, gonadotropin, growth hormone, ACTH, thyrotropin and parahormone. Prolactin is susceptible to changes in molecular aggregation or polymerization of the hormone monomer units during purification and storage. For example see Garnier et al., "J. Endocrin. and Metabolism" 47(6):1273-1281 (1978). It has also been observed by Fang et al. in "Clin. Chem." 24(6):941-943 (1978) that radioiodinated prolactin compositions containing high proportions of "small" or monomeric prolactin (MW 23,000) improve the prolactin assay sensitivity and consistency over compositions containing larger proportions of "big" prolactin (MW 170,000).

OBJECTS OF THE INVENTION

It is a principal object of this invention to reduce the nonspecific binding of radioiodinated protein hormones in immunoassays.

It is a further object of this invention to reduce such nonspecific binding in immunoassays for protein hormones such as prolactin which are capable of aggregating into polymer forms.

SUMMARY OF THE INVENTION

The above objects of the invention are achieved by storing the radioiodinated protein hormone in contact with a nonionic detergent. Use of this stabilized tracer reagent in immunoassays reduces nonspecific binding by about 25% to about 300% without interfering in the binding of tracer or analyte by immune or cell surface receptors.

The beneficial results obtained by inclusion of a nonionic detergent with the hormone are believed to flow from the stabilization of the radioiodinated hormone against aggregation, and hence changes in its ability to distribute with the insoluble fraction of the immunoassay. For example, the tracer may bind to the reaction containers, e.g. those made of nitrocellulose of polyolefins such as polypropylene, polystyrene, polyethylene or copolymers of acrylonitrile with styrene. Further, a fraction of the aggregated hormone may be of sufficiently large molecular weight that it will precipitate and be removed with the insoluble phase. This will interfere with those assay systems in which the amount of receptor-bound tracer is a measure of the original hormone concentration. A method of this type is the double antibody immunoassay. Here, a second antibody directed against anti-hormone is used to precipitate the immune complex of tracer and sample hormone with anti-hormone. The amount of bound tracer is inversely proportional to the concentration of hormone in the sample. Thus it can be seen that spurious precipitation of tracer will erroneously indicate a lower concentration of hormone than is actually present.

The nonionic detergent-tracer reagent is effective in reducing nonspecific binding, yet at the proper concentration does not adversely affect specific binding by either tracer or hormone. The proper concentration generally ranges about from 0.05 to 0.5% w/v detergent, with 0.2% being preferred; the limits chosen will depend upon the hormone receptor used in the assay, whether immune or cell surface, and the type of assay used, e.g., competitive, sandwich or double antibody. Thus the optimal concentration is determined in each system by varying the detergent concentration in the tracer composition and determining the maximum tracer binding, the extent of displacement of tracer at a given unlabelled hormone concentration (generally 20 ng/ml) and the degree of nonspecific binding. The first two determinations may be conducted in conventional fashion; an example of the last determination is disclosed in Example 1 below. The concentration that is chosen will minimize nonspecific binding, maximize the maximum binding and yield substantial tracer displacement at physiological concentrations of unlabelled hormone. Further, the displacement curve over a range of physiological concentrations desirably is as close to a straight line as possible. The aqueous solution of tracer and detergent may be stored frozen or lyophilized, but neither of these alternatives is preferred. The solution may also contain inert protein such as bovine serum albumin or other protein which cross-reacts with tracer and receptor at less than about 1%. It may also contain buffers, e.g. phosphate, and salts, e.g. sodium chloride.

Nonionic detergents are well-known and readily available commercially. Such detergents are by definition surface active but they do not contain ionogenic hydrophilic groups. Thus they are generally polyols or polyethers such as polyethylene glycol or polyethylene sorbitol which have been substituted with hydrophobic moeities. These include long chain alkyl, e.g. $C_4$ to $C_{20}$, or aryl, e.g. phenyl or alkyl-substituted phenyl. Suitable detergents include the alkylphenyl polyethylene glycol ethers such as polyethylene glycol p-isooctylphenyl ether (available commercially as Triton X-100), and the fatty acid esters of polyoxyethylene sorbitol, e.g. polyoxyethylene sorbitan monooleate (available commercially as Tween 80). Polyethylene glycol p-isooctylphenyl ether is preferred.

The stabilized tracer compositions manufactured for commercial sale or use are ordinarily stored before use for periods generally ranging from about 1 to 45 days, generally greater than 2 days. The stabilized tracer reagent is not contacted with the hormone receptor or unlabelled hormone until use in an analytical procedure. Thus it is stored essentially free of either hormone receptor or the unlabelled hormone.

The radioiodinated hormones that may be stabilized by the method of this invention include those described above which have been radioiodinated using conventional procedures. Excellent results have been obtained with $^{125}I$ prolactin made by either the chloramine-T or iodogen method. Other radioiodination methods will be apparent to the skilled artisan.

EXAMPLE 1

Prolactin was radioiodinated with $^{125}$I using chloroamine-T in accordance with the method of Hunter et al. "Nature" 194:495–496 (1962). The tracer was purified by column chromatography and the eluate mixed 1:1 with phosphate buffered saline containing 2.5% w/v bovine serum albumin. Six stabilization test buffers were prepared. All contained phosphate buffered saline, 0.02 M sodium azide as bacteriostat and 2.5% w/v bovine serum albumin. Five contained, in addition, catalase (10 μl/ml), potassium iodide (2.5% w/v), 0.03 M ethylenediaminetetraacetic acid, sodium barbital or Triton X-100 nonionic detergent (0.5% w/v). The pH of all aliquots was 6.6 except for sodium barbital, which was 7.5. Sufficient tracer solution was combined with stabilization buffers to produce a solution exhibiting about 20 to 22 thousand counts per minute. The solutions were stored in glass vials under the conditions described in Table 1. After storage the nonspecific binding was determined by conducting an immunoassay for prolactin but without the anti-prolactin antibody. This is accomplished by combining in a polypropylene test tube 50 μl of phosphate buffered saline bovine serum albumin and sodium azide (PBS), 100 μl of the stored tracer and 100 μl of normal rabbit serum, incubating for 4 hours at room temperature, mixing in 500 μl of equine anti-rabbit serum in PBS and incubating at 37° C.±2° C. for 5 minutes, centrifuging all tubes for 25 minutes at a minimum relative centrifugal force of 1500×g at 2°-25° C., decanting and counting the radioactivity remaining in the tubes. Total counts were determined by counting both the tube and its contents before decanting. The percent nonspecific binding was calculated as bound counts/total counts×100. The results are displayed in Table 1.

TABLE 1

| | | % Nonspecific Binding | | | | | | | | | |
|---|---|---|---|---|---|---|---|---|---|---|---|
| Storage Period (days) | | 2 | | | 7 | | | 14 | | 28 | |
| | Storage Temperature (°C.) | −20 | 4 | 42 | −20 | 4 | 42 | −20 | 4 | −20 | 4 |
| Storage Medium* | no additive | 5.87 | 5.07 | 5.41 | 5.61 | 7.22 | 7.63 | 6.75 | 6.38 | 7.21 | 6.97 |
| | 10 μl/ml catalase | 5.76 | 5.42 | 6.00 | 6.59 | 5.59 | 7.93 | 7.77 | 6.83 | 7.52 | 6.78 |
| | 2.5% w/v KI | 6.04 | 5.53 | 5.15 | 7.36 | 6.20 | 6.28 | 5.83 | 6.80 | 7.40 | 6.16 |
| | 0.03 M EDTA | 5.59 | 5.63 | 5.01 | 9.32 | 6.78 | 8.78 | 7.15 | 6.30 | 7.80 | 5.90 |
| | sodium barbital | 5.41 | 5.32 | 5.86 | 8.57 | 5.54 | 7.84 | 7.21 | 6.82 | 7.40 | 6.90 |
| | 0.5% w/v Triton X-100 | 4.24 | 1.90 | 2.78 | 3.44 | 3.55 | 3.33 | 3.75 | 3.79 | 3.66 | 3.94 |

*Storage media consisted of phosphate buffered saline and 2.5% w/v bovine serum albumin plus the indicated additive.

We claim:

1. In a method for the immunoassay of a hormone selected from the group consisting of prolactin, insulin, gonadotropin, growth hormone, ACTH, thyrotropin and parahormone, wherein said hormone in radioiodinated form is used as a tracer, the improvement comprising a stabilized tracer reagent consisting essentially of said radioiodinated hormone and about from 0.05 to 0.5% w/v of a nonionic detergent.

2. The immunoassay method of claim 1 wherein a receptor is used to bind the radioiodinated protein hormone.

3. The method of claim 2 wherein the receptor is an antibody.

4. The method of claim 3 wherein the antibody is immobilized by precipitation with a second antibody.

5. The method of claim 3 wherein the antibody is immobilized by adsorption to a water insoluble material.

6. The method of claim 5 wherein the material is a polyolefin.

7. The method of claim 6 wherein the polyolefin is polypropylene, polystyrene, polyethylene or a copolymer of acrylonitrile with styrene.

8. The method of claim 2 wherein the reagent is stored for a period of greater than two days.

9. The method of claim 1 wherein the nonionic detergent is an alkylarylpolyether alcohol.

10. The method of claim 9 wherein the detergent is an alkyl phenyl polyethylene glycol ether.

11. The method of claim 1 wherein the nonionic detergent is polyethoxylated poly(oxypropylene).

12. The method of claim 8 wherein the hormone is prolactin.

13. A composition consisting essentially of a radioiodinated hormone from the group consisting of prolactin, insulin, gonadotropin, growth hormone, ACTH, thyrotropin and parahormone, and about from 0.05 to 0.5% w/v of a nonionic detergent, said composition being essentially free of hormone receptor and unlabelled hormone.

14. The composition of claim 13 wherein the hormone is prolactin.

15. The composition of claim 13 further including a protein which will cross-react with antibody to the hormone at less than 1%.

16. The composition of claim 15 wherein the protein is bovine serum albumin.

17. The composition of claim 13 which is dry.

18. The composition of claim 13 which is in aqueous solution.

19. The composition of claim 18 wherein the solution comprises phosphate buffered saline at about pH 6.6.

* * * * *